US012209270B2

United States Patent
Ito et al.

(10) Patent No.: US 12,209,270 B2
(45) Date of Patent: Jan. 28, 2025

(54) KIT AND METHOD

(71) Applicant: DENKA COMPANY LIMITED, Tokyo (JP)

(72) Inventors: Yasuki Ito, Tokyo (JP); Noriyuki Satoh, Tokyo (JP)

(73) Assignee: DENKA COMPANY LIMITED, Tokyo (JP)

(*) Notice: Subject to any disclaimer, the term of this patent is extended or adjusted under 35 U.S.C. 154(b) by 378 days.

(21) Appl. No.: 17/641,774

(22) PCT Filed: Sep. 9, 2020

(86) PCT No.: PCT/JP2020/034107
§ 371 (c)(1),
(2) Date: Mar. 9, 2022

(87) PCT Pub. No.: WO2021/049527
PCT Pub. Date: Mar. 18, 2021

(65) Prior Publication Data
US 2022/0372546 A1    Nov. 24, 2022

(30) Foreign Application Priority Data
Sep. 10, 2019   (JP) .................................. 2019-164200

(51) Int. Cl.
*C12Q 1/60* (2006.01)
*C12Q 1/30* (2006.01)
*C12Q 1/44* (2006.01)

(52) U.S. Cl.
CPC ................. *C12Q 1/60* (2013.01); *C12Q 1/30* (2013.01); *C12Q 1/44* (2013.01)

(58) Field of Classification Search
None
See application file for complete search history.

(56) References Cited

U.S. PATENT DOCUMENTS

| 8,030,081 | B2 * | 10/2011 | Itoh | ......................... C12Q 1/44 436/71 |
| 8,697,378 | B2 | 4/2014 | Itoh | ................................ 435/11 |
| 9,663,816 | B2 | 5/2017 | Kuwata et al. | ................. 435/28 |
| 2009/0263844 | A1 | 10/2009 | Itoh | ................................ 435/19 |
| 2010/0035288 | A1 | 2/2010 | Itoh | ................................ 435/11 |
| 2010/0055796 | A1 | 3/2010 | Ahotupa | ......................... 436/71 |
| 2015/0079620 | A1 | 3/2015 | Kuwata et al. | ................. 435/28 |
| 2022/0299535 | A1 | 9/2022 | Itoh et al. | |

FOREIGN PATENT DOCUMENTS

| CN | 101663404 A | 3/2010 |
| EP | 1 930 442 A1 | 6/2008 |
| EP | 2 843 054 A1 | 3/2015 |
| JP | 2003-28882 A | 1/2003 |
| JP | 2003-227798 A | 8/2003 |
| JP | 2003230400 A * | 8/2003 |
| JP | 2005-278626 A | 10/2005 |
| JP | 2005-292110 A | 10/2005 |
| JP | 2013-148589 A | 8/2013 |
| WO | WO 2008/050636 A1 | 5/2008 |
| WO | WO 2008/105486 A1 | 9/2008 |
| WO | WO 2009/048143 A1 | 4/2009 |
| WO | WO 2021/049518 A1 | 3/2021 |

OTHER PUBLICATIONS

Japanese Office Action dated Sep. 5, 2023, issued by the Japanese Patent Office in corresponding application JP 2020-082162.
Extended European Search Report mailed Oct. 17, 2022, issued to European Patent Application No. 20862591.3.
Ito Yasuki et al., "Development of a homogenous assay for measurement of small dense LDL cholesterol", Clinical Chemistry, Oxford University Press, US, vol. 57, No. 1, Jan. 1, 2011 (Jan. 1, 2011), pp. 57-65.
Chinese Office Action dated Aug. 26, 2023, issued by the China National Intellectual Property Administration in corresponding application CN 202080063416.1.
International Search Report dated Dec. 1, 2020, issued by the Japanese Patent Office in corresponding application PCT/JP2020/034107.

* cited by examiner

*Primary Examiner* — Nghi V Nguyen
(74) *Attorney, Agent, or Firm* — Stein IP, LLC

(57) ABSTRACT

A kit used for fractionation of small dense LDL cholesterol (sdLDL-C) in a sample, including: a first reagent composition having one or two or more activities selected from the group consisting of cholesterol esterase activity, cholesterol oxidase activity, and sphingomyelinase activity; and a second reagent composition for quantifying the sdLDL-C, in which in an absorption spectrum after storing the first reagent composition at 37° C. for 2 weeks, a ratio R1 represented by ABS400/ABS450 is 0.90 or more and 3.00 or less, and in an absorption spectrum after storing the second reagent composition at 37° C. for 2 weeks, a ratio R1 represented by ABS400/ABS450 is 0.90 or more and 8.00 or less.

12 Claims, 4 Drawing Sheets

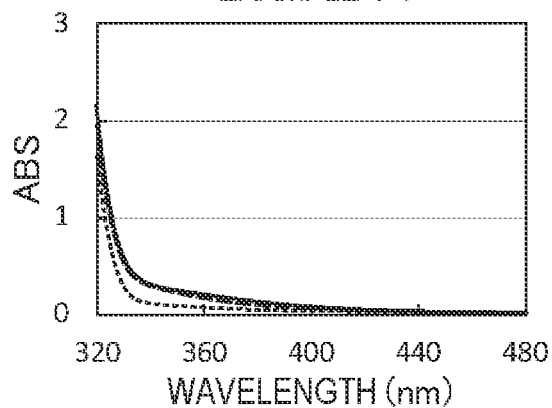
FIG. 1A EXAMPLE 1-1
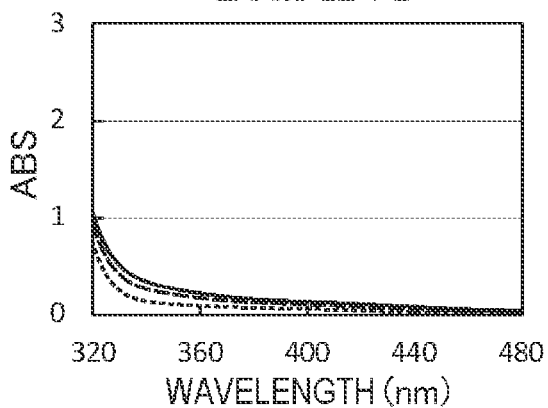
FIG. 1B EXAMPLE 1-2
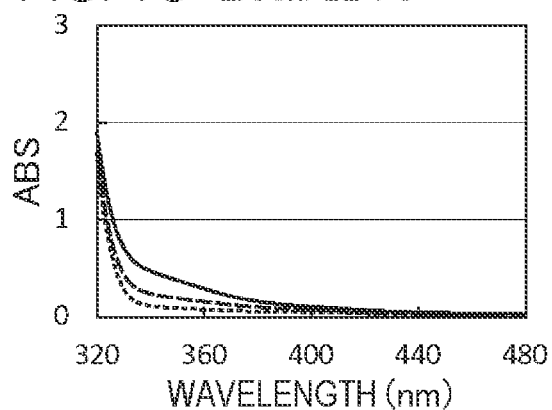
FIG. 1C EXAMPLE 1-3
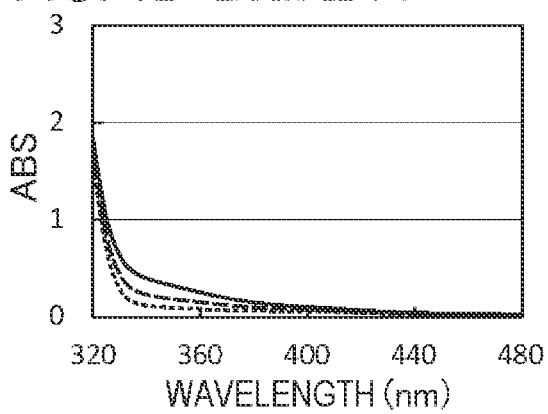
FIG. 1D EXAMPLE 1-4
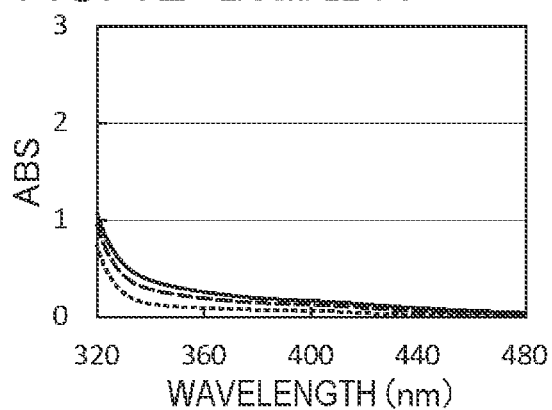
FIG. 1E EXAMPLE 1-5
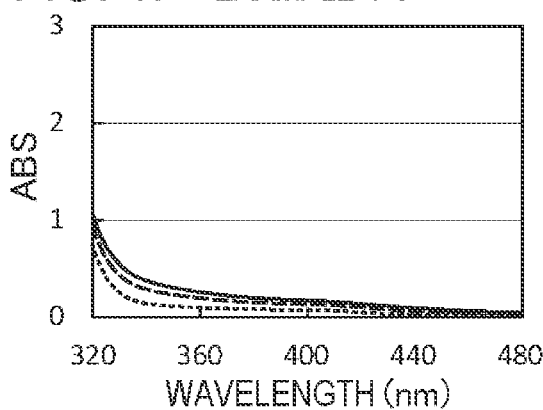
FIG. 1F EXAMPLE 1-6
---------- 0w  --------- 1w  ———— 2w

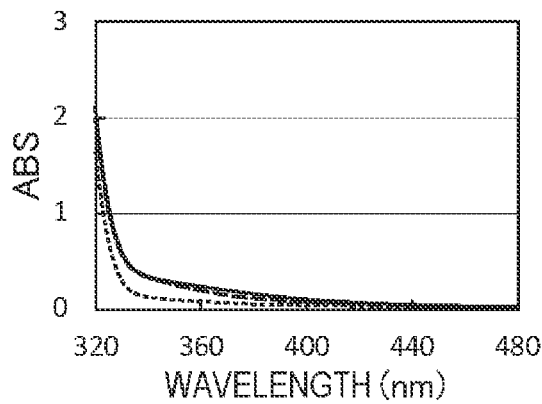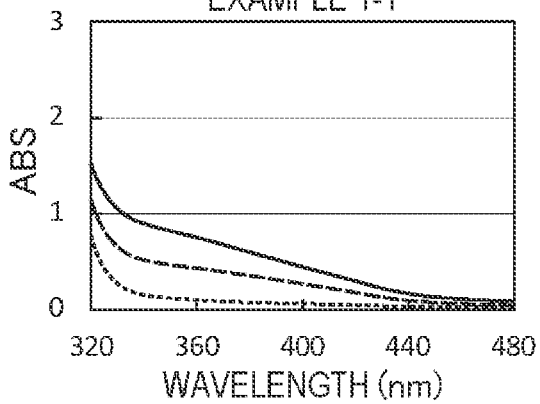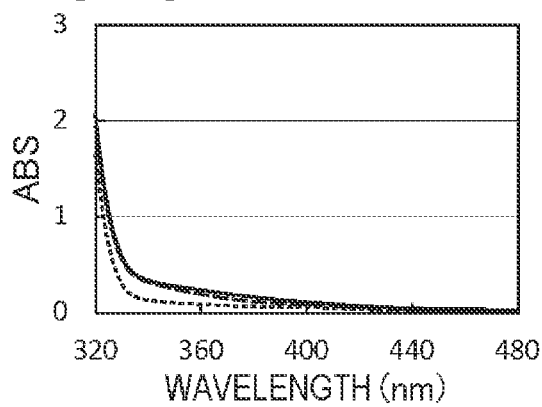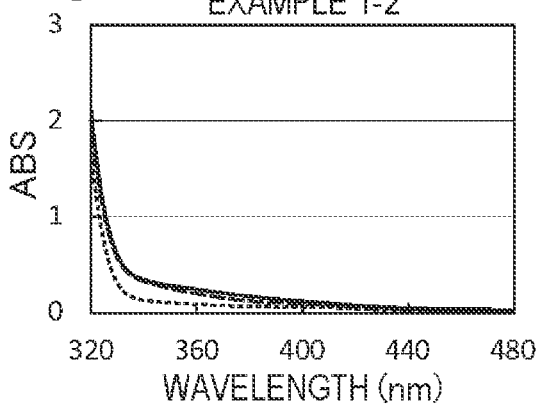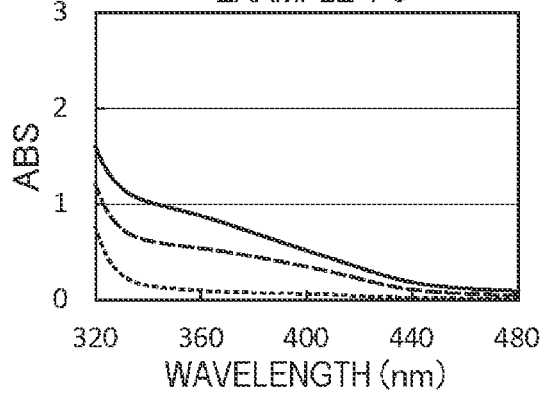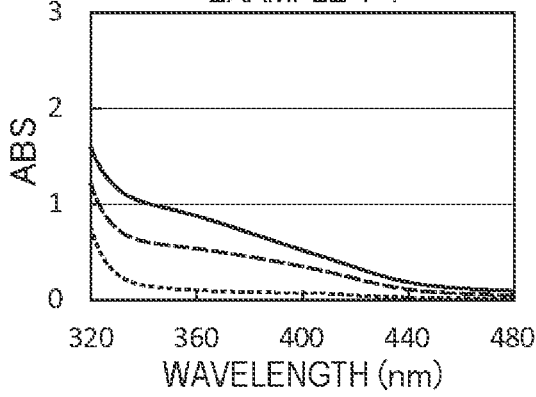

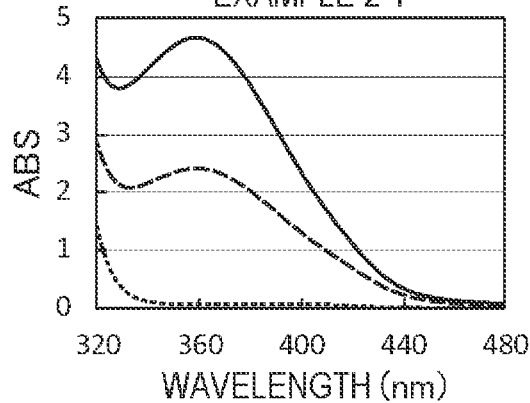
FIG. 3A COMPARATIVE EXAMPLE 2-1
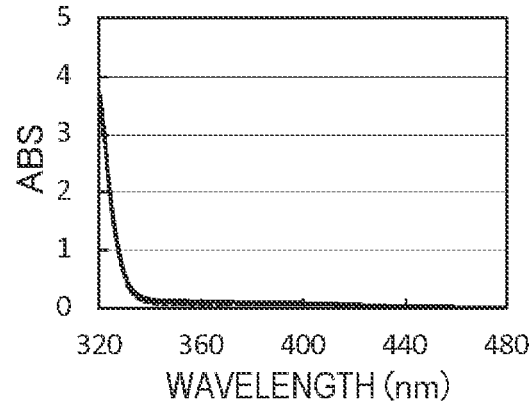
FIG. 3B EXAMPLE 2-1
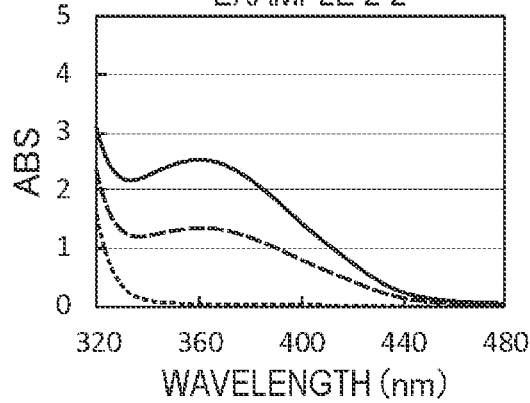
FIG. 3C COMPARATIVE EXAMPLE 2-2
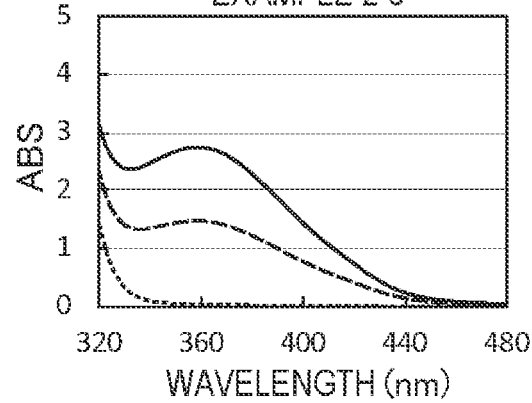
FIG. 3D COMPARATIVE EXAMPLE 2-3
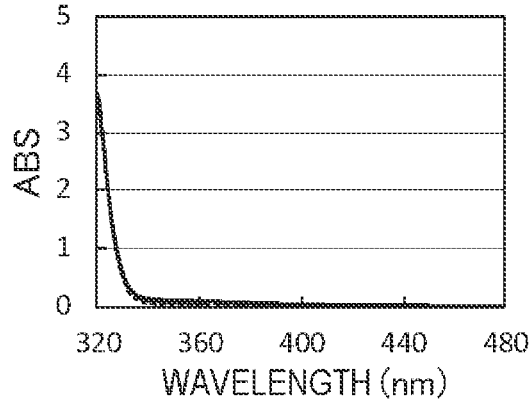
FIG. 3E EXAMPLE 2-2
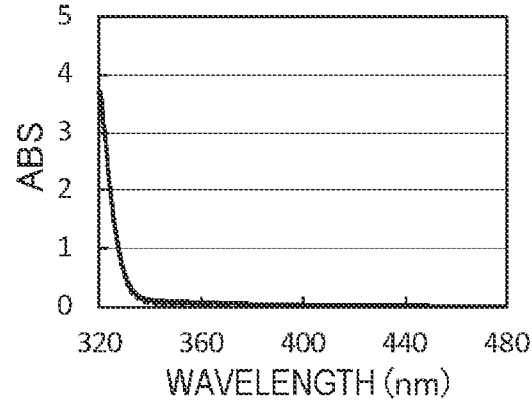
FIG. 3F EXAMPLE 2-3
·········· 0w  ——— 1w  ——— 2w FIG. 4A EXAMPLE 2-4
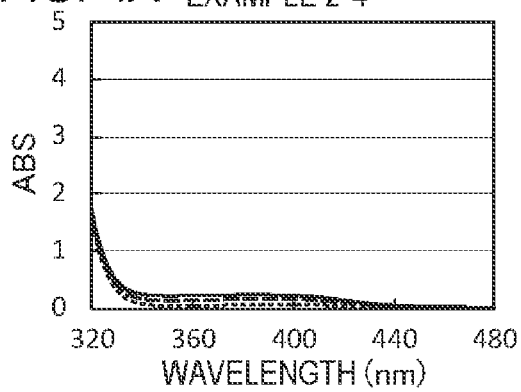
FIG. 4B EXAMPLE 2-5
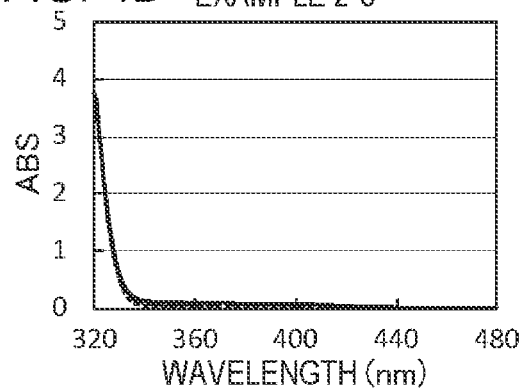
FIG. 4C EXAMPLE 2-6
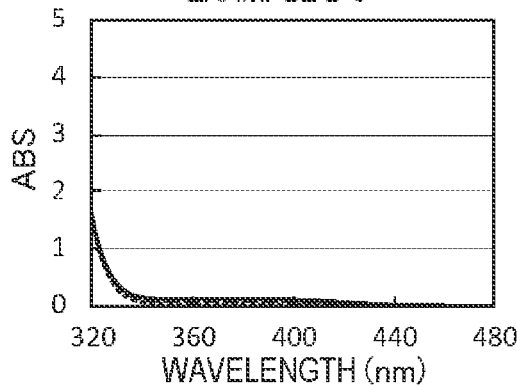
FIG. 4D EXAMPLE 2-7
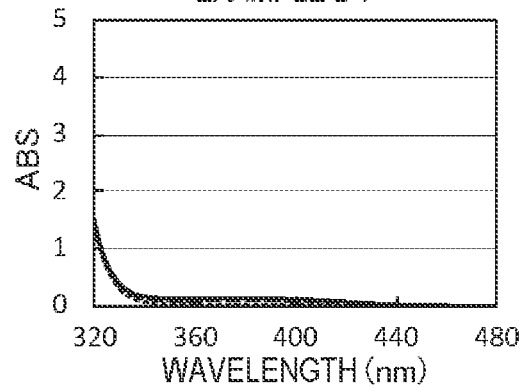
FIG. 4E EXAMPLE 2-8
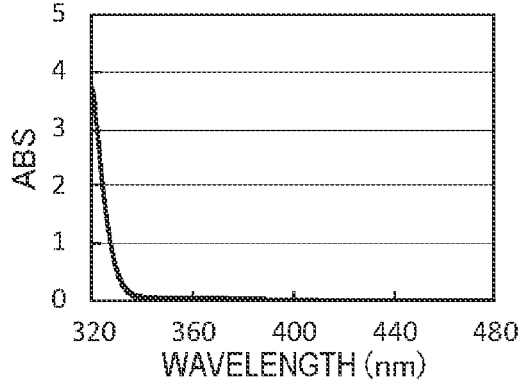
FIG. 4F EXAMPLE 2-9
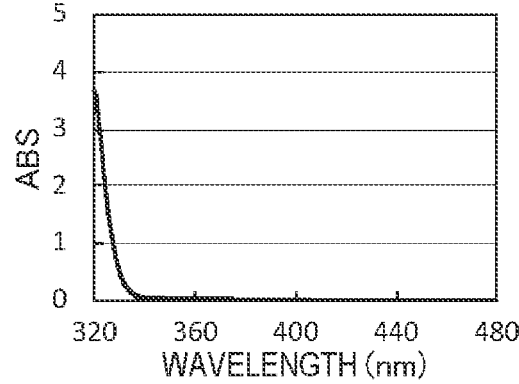
FIG. 4G COMPARATIVE EXAMPLE 2-4
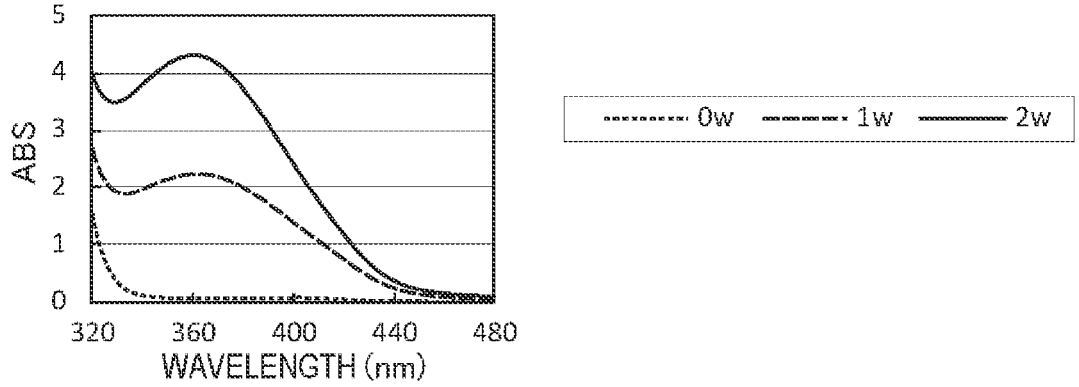
·········· 0w 1w ──── 2w

KIT AND METHOD

CROSS-REFERENCE TO RELATED APPLICATIONS

This application is a national stage of International Application No. PCT/JP2020/034107, filed Sep. 9, 2020, which claims the benefit of Japanese Application No. 2019-164200, filed Sep. 10, 2019, in the Japanese Patent Office, the disclosure of which is incorporated herein by reference.

TECHNICAL FIELD

The present invention relates to a kit and a method.

BACKGROUND ART

As a technique using measurement of absorbance and turbidity for quantifying small dense LDL cholesterol (sdLDL-C), there are methods described in Patent Documents 1 to 4.

Patent Document 1 (Japanese Unexamined Patent Publication No. 2003-28882) describes a method of measuring small dense LDL in a sample in which a monovalent cation and/or a divalent cation having a specific concentration and a polyanion are present. Then, according to the method described in the document, it is described that it is possible to provide a method of measuring small dense LDL in a sample capable of measuring only small dense LDL with specificity and high sensitivity. In addition, in the document, it is described that small dense LDL is measured by turbidity measurement at a main wavelength of 660 nm.

Patent Document 2 (Pamphlet of International Publication No. WO 2008/50636) and Patent Document 3 (Pamphlet of International Publication No. WO 2009/48143) describe that the absorbances at a main wavelength of 600 nm and a sub-wavelength of 700 nm are measured in the quantification of sdLDL-C.

In addition, Patent Document 4 (Pamphlet of International Publication No. WO 2008/105486) describes that the absorbance at 600 nm is measured in the measurement of sdLDL-C.

RELATED DOCUMENT

Patent Document

[Patent Document 1] Japanese Unexamined Patent Publication No. 2003-28882
[Patent Document 2] Pamphlet of International Publication No. WO 2008/50636
[Patent Document 3] Pamphlet of International Publication No. WO 2009/48143
[Patent Document 4] Pamphlet of International Publication No. WO 2008/105486

SUMMARY OF THE INVENTION

Technical Problem

As described above, in Patent Documents 1 to 4, when quantifying sdLDL-C, the absorbance measurement on the long wavelength side having a wavelength of about 600 to 700 nm is used.

When the present inventors have investigated such techniques, there is room for improvement in terms of stably obtaining a high level of measurement accuracy.

The present invention provides a technique for stably quantifying sdLDL-C with high accuracy.

Solution to Problem

The present inventors have investigated the quantification of sdLDL-C using absorbance measurement in a wavelength region of about 600 to 700 nm with the purpose of obtaining high measurement accuracy even for a smaller amount of sample. Then, it has been found as a new problem that in the case where a reagent used for quantification is stored, the reagent may deteriorate, absorption having a peak on a shorter wavelength side than the wavelength range in the quantification of sdLDL-C may occur, and the influence of such absorption may be observed over a high wavelength side. Then, it has been clarified that when such absorption occurs, the absorbance of sdLDL-C at the time of quantification is affected, and thus the measurement accuracy may be decreased. In addition, it has been found that the appearance of the absorption peak on the short wavelength side can be changed depending on, for example, the components of the reagent used for the measurement, the storage conditions, and the number of storage days.

Therefore, as a result of further investigation to remove the influence of absorption occurring in the short wavelength region as much as possible, it has been found that by setting the ratio of the absorbances after the reagent composition used for fractionation of sdLDL-C is subjected to an acceleration test at a specific wavelength outside the measurement wavelength region of sdLDL-C to be within a specific range, the effect of absorption on the long wavelength side can be effectively suppressed, and sdLDL-C can be quantified with high accuracy. Thus, the present invention has been completed.

According to the present invention, the following kit and method are provided.

[1] A kit used for fractionation of small dense LDL cholesterol (sdLDL-C) in a sample, including:
  a first reagent composition having one or two or more activities selected from the group consisting of cholesterol esterase activity, cholesterol oxidase activity, and sphingomyelinase activity; and
  a second reagent composition for quantifying the sdLDL-C,
  in which in an absorption spectrum after storing the first reagent composition at 37° C. for 2 weeks, when an absorbance at a wavelength of 400 nm is ABS400, and an absorbance at a wavelength of 450 nm is ABS450, a ratio R1 represented by ABS400/ABS450 is 0.90 or more and 3.00 or less, and
  in an absorption spectrum after storing the second reagent composition at 37° C. for 2 weeks, when an absorbance at a wavelength of 400 nm is ABS400 and an absorbance at a wavelength of 450 nm is ABS450, a ratio R1 represented by ABS400/ABS450 is 0.90 or more and 8.00 or less.

[2] The kit according to [1], in which in the absorption spectrum after storing the first reagent composition at 37° C. for 2 weeks, when an absorbance at a wavelength of 360 nm is ABS360, a ratio R2 represented by ABS360/ABS400 is 0.90 or more and 2.50 or less.

[3] The kit according to [1] or [2], in which the first reagent composition further has catalase activity.

[4] The kit according to any one of [1] to [3], in which the first reagent composition contains a surfactant that acts on lipoproteins other than the small dense LDL (sdLDL).

[5] The kit according to any one of [1] to [4], in which in the absorption spectrum after storing the second reagent composition at 37° C. for 2 weeks, when an absorbance at a wavelength of 360 nm is ABS360, a ratio R2 represented by ABS360/ABS400 is 0.90 or more and 2.50 or less.

[6] The kit according to any one of [1] to [5], in which the second reagent composition contains a surfactant that acts on the small dense LDL (sdLDL).

[7] The kit according to any one of [1] to [6], in which the first reagent composition satisfies one or two conditions of Conditions 1 to 3 below, and the second reagent composition does not satisfy the one or two conditions of Conditions 1 to 3 and satisfies all other conditions:
Condition 1: containing a coupler;
Condition 2: containing an iron complex; and
Condition 3: having peroxidase activity.

[8] A method of quantifying small dense LDL cholesterol (sdLDL-C) in a sample, including:

a step of allowing a first reagent composition having one or two or more activities selected from the group consisting of cholesterol esterase activity, cholesterol oxidase activity, and sphingomyelinase activity to act on the sample; and a step of, after the step of allowing the first reagent composition to act on the sample, allowing a second reagent composition for quantifying the sdLDL-C to act to quantify cholesterol in a remaining lipoprotein, in which in an absorption spectrum after storing the first reagent composition at 37° C. for 2 weeks, when an absorbance at a wavelength of 400 nm is ABS400, and an absorbance at a wavelength of 450 nm is ABS450, a ratio R1 represented by ABS400/ABS450 is 0.90 or more and 3.00 or less, and in an absorption spectrum after storing the second reagent composition at 37° C. for 2 weeks, when an absorbance at a wavelength of 400 nm is ABS400 and an absorbance at a wavelength of 450 nm is ABS450, a ratio R1 represented by ABS400/ABS450 is 0.90 or more and 8.00 or less.

[9] The method according to [8], in which in the absorption spectrum after storing the first reagent composition at 37° C. for 2 weeks, when an absorbance at a wavelength of 360 nm is ABS360, a ratio R2 represented by ABS360/ABS400 is 0.90 or more and 2.50 or less.

[10] The method according to [8] or [9], in which the first reagent composition further has catalase activity.

[11] The method according to any one of [8] to [10], in which the first reagent composition contains a surfactant that acts on lipoproteins other than the sdLDL.

[12] The method according to any one of [8] to [11], in which in the absorption spectrum after storing the second reagent composition at 37° C. for 2 weeks, when an absorbance at a wavelength of 360 nm is ABS360, a ratio R2 represented by ABS360/ABS400 is 0.90 or more and 2.50 or less.

[13] The method according to any one of [8] to [12], in which the second reagent composition contains a surfactant that acts on the sdLDL.

[14] The method according to any one of [8] to [13], in which the first reagent composition satisfies one or two conditions of Conditions 1 to 3 below, and the second reagent composition does not satisfy the one or two conditions of Conditions 1 to 3 and satisfies all other conditions:
Condition 1: containing a coupler;
Condition 2: containing an iron complex; and
Condition 3: having peroxidase activity.

Advantageous Effects of Invention

According to the present invention, it is possible to provide a technique for stably quantifying sdLDL-C with high accuracy.

BRIEF DESCRIPTION OF THE DRAWINGS

FIGS. 1A to 1F are diagrams showing examples of absorbance measurement results of first reagent compositions.

FIGS. 2A to 2F are diagrams showing examples of absorbance measurement results of the first reagent compositions.

FIGS. 3A to 3F are diagrams showing examples of absorbance measurement results of second reagent compositions.

FIGS. 4A to 4G are diagrams showing examples of absorbance measurement results of second reagent compositions.

DESCRIPTION OF EMBODIMENTS

Hereinafter, embodiments will be described. In the embodiment, the composition such as the measurement reagent may contain each component alone or in combination of two or more. In addition, in the present specification, "x to y" in the numerical range represents "x or more and y or less", and includes both a lower limit value x and an upper limit value y.

First, a lipoprotein will be described.

A lipoprotein can be fractionated roughly into Very Low Density Lipoprotein (VLDL), Low Density Lipoprotein (LDL) and High Density Lipoprotein (HDL), and LDL is sub-fractionated into a small dense LDL (sdLDL), and other sub-fractions. sdLDL is also referred to as small particle LDL, small LDL (SLDL), dense LDL, small and dense LDL, and other LDLs are sometimes referred to as large LDL (L LDL) or light LDL.

These lipoprotein fractions and sub-fractions may be distinguished based on particle size or specific gravity.

The particle size of lipoprotein in diameter is, 30 nm to 80 nm (or 30 nm to 75 nm) for VLDL, 22 nm to 28 nm (or 19 nm to 30 nm) for LDL, and 7 nm to 10 nm for HDL, although the figures may vary depending on the researchers.

The specific gravity of lipoprotein is, for example, 1.006 or less for VLDL, 1.019 to 1.063 for LDL, and 1.063 to 1.21 for HDL.

Among lipoproteins, the diameter of LDL particles can be measured by, for example, gradient gel electrophoresis (GGE) (JAMA, 260, p. 1917-21, 1988) or NMR (HANDBOOK OF LIPOPROTEIN TESTING 2nd Edition, Edited by Nader Rifai et al. p. 609-623, AACC PRESS: The Fats of Life Summer 2002, LVDD 15 YEAR ANNIVERSARY ISSUE, Volume AVI No. 3, p. 15-16). The specific gravity can be determined based on, for example, analysis by ultracentrifugation (Atherosclerosis, 106, p. 241-253, 1994: Atherosclerosis, 83, p. 59, 1990).

In the embodiment, the sdLDL to be measured generally refers to a sub-fraction having a diameter of about 22.0 to about 25.5 nm or a sub-fraction having a specific gravity of 1.040 to 1.063 among LDL fractions.

The reason why LDL is sub-fractionated according to the particle size is that a small LDL among LDLs needs to be fractionally measured since LDL with a small particle diameter causes more arteriosclerosis and is higher in malignancy than other LDLs. Since the distributions of diameter and specific gravity of a LDL are continuous, it is not possible to determine the value of specific gravity above which the malignancy is clearly higher. Therefore, the specific gravity value of 1.040 to 1.063 described above is not an established characteristic of sdLDL, but is a value on the high specific gravity side obtained by dividing the specific gravity range of 1.019 to 1.063, which is widely used and established as the specific gravity of LDL, at a median point. For example, regarding the specific gravity of sdLDL, in a different report, sdLDL is fractionated in a range of 1.044 to 1.060 (Atherosclerosis: 106 241-253 1994). There are some differences among researchers on how to set the range of the specific gravity of sdLDL, but with any of the ranges chosen, the presence of sdLDL is associated with clinical malignancy.

In the present specification, specifically, a sdLDL is defined as an LDL having a large specific gravity among LDLs and with a higher association with arteriosclerosis clinically than other LDLs. In addition, preferably, the sdLDL has a specific gravity range greater than the median point within the range of specific gravity for LDLs, and more preferably, the sdLDL refers to an LDL with the specific gravity in a range of 1.044 to 1.063. Further, lipoproteins other than LDL refer to VLDL or HDL, and include chylomicrons, intermediate density lipoproteins (IDL), or very high density lipoproteins (VHDL).

(Kit)

In the embodiment, a kit is used for fractionation of sdLDL-C in a sample, and includes a first reagent composition and a second reagent composition below.

(First Reagent Composition)

The first reagent composition is a reagent composition having one or two or more activities selected from the group consisting of cholesterol esterase activity, cholesterol oxidase activity, and sphingomyelinase activity. In an absorption spectrum after storing the first reagent composition at 37° C. for 2 weeks, when an absorbance at a wavelength of 400 nm is ABS400 and an absorbance at a wavelength of 450 nm is ABS450, a ratio R1 represented by ABS400/ABS450 is 0.9 or more and 3.0 or less.

(Second Reagent Composition)

The second reagent composition is a reagent composition for quantifying the sdLDL-C. In an absorption spectrum after storing the second reagent composition at 37° C. for 2 weeks, when an absorbance at a wavelength of 400 nm is ABS400 and an absorbance at a wavelength of 450 nm is ABS450, a ratio R1 represented by ABS400/ABS450 is 0.90 or more and 8.00 or less.

The present inventors have newly found that sdLDL-C can be quantified with high accuracy by setting the ratio of the absorbances of the first and second reagent compositions after the acceleration test to a specific range at a specific wavelength which is outside the measurement wavelength region of sdLDL-C. Specifically, it has been found that a ratio R1 of ABS400/ABS450 is suitable as an index for the presence or absence and the degree of absorption on the short wavelength side. By setting R1 to the upper limit value or smaller, interference to the measurement wavelength range of sdLDL-C, for example, an absorption wavelength region of 600 to 700 nm, from an adsorption having a peak on the lower wavelength side than the wavelength region of 600 to 700 nm can be effectively suppressed. Thus, sdLDL-C can be quantified with high accuracy.

Here, although it is difficult to determine the presence or absence of interference in the measurement wavelength range of sdLDL-C itself, the existence of absorption having a peak on the low wavelength side and the influence of interference can be understood by using the absorbances at 400 nm and 450 nm outside the observation region and using the absorbance ratio of the first and second reagent compositions after the acceleration test as an index. Then, the measurement accuracy can be improved by using the reagent composition in which R1 is within a specific range.

Regarding the first reagent composition, in an absorption spectrum after storing the first reagent composition at 37° C. for 2 weeks, when an absorbance at a wavelength of 400 nm is ABS400 and an absorbance at a wavelength of 450 nm is ABS450, a ratio R1 represented by ABS400/ABS450 is 3.00 or less, preferably 2.80 or less, more preferably 2.70 or less, even more preferably 2.60 or less, and still even more preferably 2.50 or less from the viewpoint of improving the measurement accuracy of sdLDL-C.

In addition, from the viewpoint of stably quantifying sdLDL-C, the R1 of the first reagent composition is 0.90 or more, and may be, for example, 0.95 or more or 1.00 or more.

Regarding the second reagent composition, in an absorption spectrum after storing the second reagent composition at 37° C. for 2 weeks, when an absorbance at a wavelength of 400 nm is ABS400 and an absorbance at a wavelength of 450 nm is ABS450, a ratio R1 represented by ABS400/ABS450 is 8.00 or less, preferably 7.00 or less, more preferably 6.00 or less, even more preferably 5.00 or less, and still even more preferably 4.00 or less from the viewpoint of improving the measurement accuracy of sdLDL-C.

In addition, from the viewpoint of stably quantifying sdLDL-C, the R1 of the second reagent composition is 0.90 or more, and may be, for example, 0.95 or more or 1.00 or more.

In the embodiment, since both the first and second reagent compositions included in the kit satisfy the above conditions for R1, sdLDL-C can be measured with high accuracy.

In addition, in the kit according to the embodiment, in the absorption spectrum of at least one of the first and second reagent compositions after storing the reagent composition at 37° C. for 2 weeks, when an absorbance at a wavelength of 360 nm is ABS360, a ratio R2 represented by ABS360/ABS400 is 2.50 or less, preferably 2.00 or less, more preferably 1.80 or less, even more preferably 1.70 or less, and still even more preferably 1.50 or less from the viewpoint of more stably improving the measurement accuracy of sdLDL-C.

In addition, from the viewpoint of more stably quantifying sdLDL-C, for example, the R2 may be 0.9 or more, and may be, for example, 1.0 or more or 1.2 or more, for example.

In addition, regarding the first reagent composition, in the absorption spectrum of the first reagent composition after storing the first reagent composition at 37° C. for 2 weeks, when an absorbance at a wavelength of 360 nm is ABS360, a ratio R2 represented by ABS360/ABS400 is, for example, 3.0 or less, preferably 2.50 or less, more preferably 2.20 or less, even more preferably 2.00 or less, still even more preferably 1.68 or less, and even much more preferably 1.60 or less from the viewpoint of more stably improving the measurement accuracy of sdLDL-C.

In addition, from the viewpoint of more stably quantifying sdLDL-C, for example, the R2 of the first reagent composition may be 0.90 or more, and may be, for example, 0.95 or more or 1.00 or more.

In addition, regarding the second reagent composition, in the absorption spectrum of the second reagent composition after storing the second reagent composition at 37° C. for 2 weeks, when an absorbance at a wavelength of 360 nm is ABS360, a ratio R2 represented by ABS360/ABS400 is, for example, 3.00 or less, preferably 2.50 or less, more preferably 2.00 or less, even more preferably 1.70 or less, and still even more preferably 1.50 or less from the viewpoint of more stably improving the measurement accuracy of sdLDL-C.

In addition, from the viewpoint of more stably quantifying sdLDL-C, the R2 of the second reagent composition may be, for example, 0.90 or more, and may be, for example, 0.95 or more or 1.00 or more.

From the viewpoint of further improving the measurement accuracy of sdLDL-C, more preferably, both the first and second reagent compositions satisfy the above conditions for R2.

In this embodiment, the kit is used for fractionation or quantification of sdLDL-C, and preferably used for fractionation and quantification of sdLDL-C.

In addition, the kit is specifically used for a method of quantifying sdLDL-C including two or more steps. At this time, the first and second reagent compositions are used in different steps, and preferably the first and second reagent compositions are used in this order.

Hereinafter, the composition of each reagent composition will be described in more detail.

(First Reagent Composition)

The first reagent composition has one or two or more activities selected from the group consisting of cholesterol esterase activity, cholesterol oxidase activity, and sphingomyelinase activity, and preferably has cholesterol esterase activity, cholesterol oxidase activity, and sphingomyelinase activity.

Since the first reagent composition is a composition having one or two or more activities of the above-mentioned activities, when the first reagent composition is added to the sample, for example, lipoproteins other than sdLDL in the sample can be removed. In addition, cholesterol in lipoproteins other than sdLDL can be led to the outside of the reaction system.

The first reagent composition is, for example, a composition containing one or two or more enzymes having one or two or more activities selected from the group consisting of cholesterol esterase activity, cholesterol oxidase activity, and sphingomyelinase activity, and preferably includes an enzyme having cholesterol esterase activity, an enzyme having cholesterol oxidase activity, and an enzyme having sphingomyelinase activity.

Here, the expression "the surfactant acts (reacts)" means that the surfactant degrades the lipoprotein and the cholesterol in the lipoprotein is liberated. For example, in the case of "surfactant that acts (reacts) on lipoproteins other than sdLDL", it is not required that the surfactant does not act on sdLDL at all, and the surfactant may mainly act on lipoproteins other than sdLDL. The term "removal" means that a substance in a test sample is degraded so as to prevent the degraded product from being detected in the subsequent step. That is, the expression "remove cholesterol in lipoproteins other than sdLDL" means that lipoproteins other than sdLDL in the test sample are degraded so as to avoid the cholesterol in the lipoproteins, which is a degraded product, not being detected in the subsequent step.

Specifically, the expression "led to the outside of the reaction system" means that cholesterol contained in HDL, VLDL, L LDL, and the like is removed or aggregated together so as to avoid the cholesterol contained in HDL. VLDL. L LDL, and the like affecting the quantification of sdLDL-C, or the cholesterol contained in HDL, VLDL, L LDL, and the like is inhibited so as to avoid the reaction thereof in the subsequent step.

In addition, specifically, the expression "having cholesterol esterase activity" means that cholesterol esterase is present and a reaction catalyzed by peroxidase cholesterol esterase may occur. The same applies to other enzyme activities such as cholesterol oxidase activity, sphingomyelinase activity, catalase activity, and peroxidase activity.

In addition, it is preferable that the first reagent composition further has catalase activity from the viewpoint of more stably leading cholesterol in lipoproteins other than sdLDL in the sample to the outside of the reaction system. More specifically, the first reagent composition is preferably a composition further containing one or two or more enzymes having catalase activity.

Next, the components contained in the first reagent composition will be described in more detail.

Examples of the components contained in the first reagent composition include an enzyme, a protein having no enzymatic action, a surfactant, a buffer solution, a coupler, an electron donor, and an iron complex.

Examples of the enzyme include an enzyme having one or two or more activities selected from the group consisting of cholesterol esterase activity, cholesterol oxidase activity, and sphingomyelinase activity. In addition, an enzyme having an activity other than the above-mentioned activity may be contained. For example, the first reagent composition preferably further has catalase activity, and more preferably contains an enzyme having catalase.

Specific examples of the enzyme include cholesterol esterase, cholesterol oxidase, sphingomyelinase, catalase, and peroxidase.

Among these, as the cholesterol esterase, for example, those derived from bacteria or fungi can be used.

As the cholesterol oxidase, for example, those derived from bacteria or yeast can be used.

Specific examples of sphingomyelinase include SPC (manufactured by Asahi Kasei Corporation), Sphingomyelinase from *Bacillus cereus*, and Sphingomyelinase from *Staphylococcus aureus* (manufactured by SIGMA).

In addition, regarding the enzyme activity in the first reagent composition, for example, the sphingomyelinase activity is preferably 0.1 U/mL or more, and more preferably 0.2 U/mL or more, and preferably 100 U/mL or less, and more preferably 20 U/mL or less from the viewpoint of more stably leading cholesterol in lipoproteins other than sdLDL to the outside of the reaction system.

In addition, the first reagent composition may preferably contain a lipoprotein degrading enzyme from the viewpoint of preferably adjusting the action on various lipoproteins.

As the lipoprotein degrading enzyme, for example, lipoprotein lipase may be used. The lipoprotein lipase is not limited as long as the lipoprotein lipase is an enzyme capable of degrading lipoproteins, and for example, animal- or microorganism-derived lipoprotein lipase may be used.

As a specific example of a protein having no enzymatic action, albumin can be used.

Examples of the surfactant include surfactants that act on lipoproteins other than sdLDL, and more preferably surfactants that act on lipoproteins other than sdLDL and do not act on sdLDL. Further, the first reagent composition preferably contains a surfactant that acts on lipoproteins other than sdLDL and more preferably contains a surfactant that acts on lipoproteins other than sdLDL and does not act on sdLDL from the viewpoint of stably fractionating sdLDL-C.

Examples of the surfactant that acts on lipoproteins other than sdLDL include polyoxyethylene derivatives. Examples of the derivatives include one or two or more nonionic surfactants selected from the group consisting of polyoxyethylene alkyl ether and polyoxyethylene polycyclic phenyl ether.

Among these, preferable examples of the polyoxyethylene polycyclic phenyl ether include a polyoxyethylene benzyl phenyl derivative, a polyoxyethylene styrenated phenyl ether derivative, and a special phenol ethoxylate. Specific examples of the polyoxyethylene polycyclic phenyl ether include Emulgen A-60, Emulgen A-500, Emulgen B-66, and Emulgen A-90 (all manufactured by Kao Corporation), Newcol 703, Newcol 704, Newcol 706, Newcol 707, Newcol 708, Newcol 709, Newcol 710, Newcol 711, Newcol 712, Newcol 714, Newcol 719, Newcol 723. Newcol 729. Newcol 733, Newcol 740, Newcol 747, Newcol 780, Newcol 610, Newcol 2604, Newcol 2607, Newcol 2609, and Newcol 2614 (all manufactured by Nippon Nyukazai Co., Ltd.), Neugen EA-87, Neugen EA-137, Neugen EA-157, Neugen EA-167, Neugen EA-177, Neugen EA-197D, and Neugen EA-207D (all manufactured by Daiichi Kogyo Seiyaku Co., Ltd.), and Blaunon DSP-9, Blaunon DSP-12.5, Blaunon TSP-7.5, Blaunon TSP-16, and Blaunon TSP-50 (all manufactured by Aoki Oil Industrial Co., Ltd.).

The concentration of the surfactant in the first reagent composition is preferably 0.2% (w/v) or more, more preferably 0.3% (w/v) or more, and even more preferably 0.5% (w/v) or more with respect to the total composition of the first reagent composition from the viewpoint of causing the surfactant to stably act on lipoproteins other than sdLDL.

In addition, from the same viewpoint, the concentration of the surfactant in the first reagent composition is preferably 5% (w/v) or less, and more preferably 3% (w/v) or less.

The surfactant contained in the first and second reagent compositions can be identified by a method of analysis by combining IR, NMR, LC-MS and the like. Examples of a method of confirming the ionicity (nonionicity, anionicity, cationicity) of the surfactant include an extraction method using an organic solvent under acidic or alkaline conditions and a solid phase extraction method. Examples of a method of determining the structure of the surfactant include a method of analysis using LC-MSMS and NMR.

The first reagent composition preferably contains an enzyme and a surfactant, more preferably contains sphingomyelinase and a polyoxyethylene derivative.

The type of buffer solution can be appropriately selected depending on, for example, the type of enzyme contained in the first reagent composition. Specific examples of the buffer solution include a phosphate buffer solution, a TRIS buffer solution, and a PIPES buffer solution.

A coupler and an electron donor are used, for example, in combination to cause a coupling reaction in the presence of peroxidase activity.

Examples of the coupler used in such a coupling reaction include 4-aminoantipyrine, an aminoantipyrine derivative, vanillindiamine sulfonic acid, methylbenzothiazolinone hydrazone, and sulfonated methylbenzothiazolinone hydrazone.

The electron donor is preferably an aniline derivative. Specific examples of the aniline derivative include N-ethyl-N-(2-hydroxy-3-sulfopropy)-3-methylaniline (TOOS), N-ethyl-N-(2-hydroxy-3-sulfopropyl)-3,5-dimethylaniline (MAOS), N-ethyl-N-(3-sulfopropyl)-3-methylaniline (TOPS), N-(2-hydroxy-3-sulfopropyl)-3,5-dimethoxyaniline (HDAOS), N-(3-sulfopropyl)aniline (HALPS), and N-(3-sulfopropy)-3-methoxy-5-aniline (HMMPS).

Further, as the iron complex, for example, those described later for the second reagent composition may be used. The concentration of the iron complex is preferably 0.001 to 0.05 mmol/L.

The first reagent composition may contain, for example, sphingomyelinase, and may also contain, for example, an enzyme that degrades cholesterol such as cholesterol esterase or cholesterol oxidase, either an electron donor or a coupler, catalase that removes hydrogen peroxide, and the like.

(Second Reagent Composition)

The second reagent composition is a reagent for quantifying the sdLDL-C. The components of the second reagent composition differ depending on the composition of the first reagent composition, any formulation composition capable of quantifying sdLDL-C may be used, and known substances can be used.

Examples of the components of the second reagent composition include an enzyme, a buffer solution, a surfactant, a coupler, and an iron complex.

Examples of the enzyme include peroxidase.

The type of buffer solution can be appropriately selected depending on, for example, the type of enzyme contained in the second reagent composition. Specific examples of the buffer solution include those described above for the first reagent composition.

Examples of the surfactant include surfactants that act on sdLDL. In addition, the second reagent composition preferably contains a surfactant that acts on sdLDL from the viewpoint of stably quantifying sdLDL-C.

The surfactant that acts on sdLDL may be a surfactant that selectively acts on sdLDL, such as a surfactant that acts only on sdLDL, or a surfactant that also acts on lipoproteins other than sdLDL, or a surfactant that acts on all lipoproteins.

As the surfactant that acts only on sdLDL, for example, a polyoxyethylene-polyoxypropylene copolymer or a derivative thereof may be suitably used. Examples of the polyoxyethylene-polyoxypropylene copolymer or the derivative thereof include Pluronic (registered trademark) series surfactants such as Pluronic 17R-4, Pluronic L-64, Pluronic PE3100, Pluronic P-85, Pluronic F-88, Pluronic P-103, and Pluronic F-127 (manufactured by BASF and ADEKA Corporation).

As a surfactant that acts on all lipoproteins, for example, a polyoxyethylene derivative may be mentioned, and any commercially available surfactant may be used as long as the surfactant is used in reagents or the like for total cholesterol measurement. Examples of such a surfactant include polyoxyethylene alkyl phenyl ether (for example, Emulgen 909 (manufactured by Kao Corporation), and Triton X100) and polyoxyethylene alkyl ether (for example, Emulgen 707 and Emulgen 709 (manufactured by Kao Corporation)).

The concentration of the surfactant in the second reagent composition is preferably 0.05% or more, more preferably 0.1% (w/v) or more, and even more preferably 0.5% (w/v) or more with respect to the total composition of the second reagent composition from the viewpoint of causing the surfactant to stably act on sdLDL.

In addition, from the same viewpoint, the concentration of the surfactant in the second reagent composition is preferably 8.0% (w/v) or less, and more preferably 5.0% (w/v) or less.

Examples of the coupler include those described above for the first reagent composition.

Examples of the iron complex include potassium ferrocyanide, sodium ferrocyanide, porphyrin iron complex, and EDTA-iron complex.

The concentration of the iron complex in the second reagent composition is preferably 0.0015 mmol/L or more, and preferably 0.3 mmol/L or less with respect to the total composition of the second reagent composition, and may be, for example, 0.05 mmol/L or less.

In addition, it is preferable that the first reagent composition satisfies one or two conditions of Conditions 1 to 3 below, and the second reagent composition does not satisfy the one or two conditions satisfied by the first reagent composition among Conditions 1 to 3, and satisfies all other conditions:

Condition 1: containing a coupler;
Condition 2: containing an iron complex; and
Condition 3: having peroxidase activity.

In the quantification of sdLDL-C, for example, the absorbance at a specific wavelength is measured using dye formed by the coupling reaction of the electron donor and the coupler in the presence of peroxidase activity. At this time, an iron complex may be used as a reaction accelerator, but when the coupler, the peroxidase activity, and the iron complex are present in the same reagent, the reagent gradually may develop a natural color and affects the quantification of sdLDL-C. In this regard, by making the first and second reagent compositions have the above-mentioned composition, the coupler, the peroxidase activity and the iron complex can be prevented from coexisting in the first or second reagent composition, and thus the natural color development of the reagent composition can be suppressed. Therefore, the quantification of sdLDL-C can be more stably performed.

From the viewpoint of more stable quantification of sdLDL-C, it is more preferable that the first reagent composition satisfies Conditions 1 and 3, and the second reagent composition satisfies Condition 2.

From the same viewpoint, it is also preferable that the coupler and the electron donor are separately present in separate reagent compositions.

In addition, serum albumin may be contained in the first or second reagent composition.

The pH of each reagent composition is around neutral pH, and is within a range of, for example, pH6 to pH8, and preferably within a range of pH6.5 to pH7.5. The pH may be adjusted by addition of a buffer solution.

(Method)

A method in the embodiment is a method of quantifying sdLDL-C in a sample using the above-mentioned first and second reagent compositions. The quantification method in the embodiment includes the following first step and second step.

(First Step) A step of allowing the above-mentioned first reagent composition to act on a sample.
(Second Step) After the first step, a step of allowing the above-mentioned second reagent composition to act to quantify cholesterol in the remaining lipoprotein.

The composition of the first and second reagent compositions is as described above.

In such a method, sdLDL-C can be stably quantified with high accuracy by using the first and second reagent compositions in which the absorbance ratio R1 satisfies the above-mentioned conditions.

In addition, the quantification method of sdLDL-C may be performed by, for example, adding the first reagent composition to a sample (test sample) for reaction, then adding the second reagent composition to the sample for reaction, and measuring the absorbance.

The test sample is, for example, serum or blood plasma, and preferably serum.

The first and second steps are usually performed in an autoanalyzer.

The amount of the sample and the amount of each reagent composition can be appropriately determined in consideration of, for example, the concentration of the reagent in each reagent composition or the like, but the steps are performed within a range applicable to the autoanalyzer. For example, 1 to 10 μL of the test sample, 50 to 300 μL of the first reagent, and 25 to 200 μL of the second reagent may be used.

Hereinafter, each step will be described in more detail.

(First Step)

In the first step, the first reagent composition is allowed to act on the sample. By doing this, lipoproteins other than sdLDL are removed, and cholesterol in the lipoproteins other than sdLDL is liberated and led to the outside of the reaction system.

More specifically, in the first step, preferably, a surfactant that acts on lipoproteins other than the sdLDL is allowed to act on the sample in the presence of sphingomyelinase and cholesterol esterase. Then, cholesterol generated by liberation from lipoproteins is allowed to react with an enzyme that reacts with cholesterol, such as cholesterol oxidase, and is led to the outside of the reaction system. In the first step, for example, known techniques for removing cholesterol in lipoproteins other than sdLDL and leading the cholesterol to the outside of the reaction system, aggregating cholesterol in lipoproteins other than sdLDL, inhibiting cholesterol in lipoproteins other than sdLDL to avoid the reaction in the subsequent step, and the like can be used.

For example, when the first reagent composition has sphingomyelinase activity, the sphingomyelinase activity of the reaction solution in the first step is preferably 0.05 U/mL or more, and more preferably 0.1 U/mL or more, and preferably 100 U/mL or less, and more preferably 20 U/mL or less from the viewpoint of selectively removing lipoproteins other than sdLDL.

Further, for example, when the first reagent composition contains a surfactant that reacts with lipoproteins other than sdLDL, the concentration of the surfactant in the reaction solution in the first step is preferably 0.15% (w/v) or more, and more preferably 0.25% (w/v) or more, and preferably 5% (w/v) or less, and more preferably 3% (w/v) or less from the viewpoint of selectively removing lipoproteins other than sdLDL.

In the first step, the step of removing cholesterol generated from lipoproteins other than sdLDL and leading the cholesterol to the outside of the reaction system can be preferably performed by any of the following methods.

(1) A method of producing hydrogen peroxide from cholesterol in lipoproteins other than sdLDL by cholesterol esterase activity and cholesterol oxidase activity, and degrading the hydrogen peroxide into water and oxygen in the presence of catalase activity.
(2) A method of forming a colorless quinone in the presence of hydrogen peroxide generated by cholesterol esterase activity and cholesterol oxidase activity, and a coupler or an electron donor.
(3) A method of degrading hydrogen peroxide in the presence of catalase activity and simultaneously forming a colorless quinone in the presence of a coupler or an electron donor.

In the above methods, the first reagent composition has one or two or more activities selected from the group consisting of cholesterol esterase activity, cholesterol oxidase activity, and sphingomyelinase activity, and has, for example, the following composition.

In the case of the method (1) above, the first reagent composition further has catalase activity.

In the case of the method (2) above, the first reagent composition contains at least one of a coupler and an electron donor, and the first reagent composition further has peroxidase activity.

In the case of the method (3) above, the first reagent composition has catalase activity and peroxidase activity, and the first reagent composition contains a coupler or an electron donor.

In the above method (1) or (2), cholesterol esterase and cholesterol oxidase are allowed to act on cholesterol to generate hydrogen peroxide, and the generated hydrogen peroxide is removed.

The concentration of the cholesterol esterase in the reaction solution is preferably 0.010 U/mL or more, more preferably 0.3 U/mL or more, and even more preferably 0.6 U/mL or more, and preferably 10 U/mL or less, more preferably 2.5 U/mL or less, and even more preferably 2.0 U/mL or less.

In addition, the concentration of cholesterol oxidase in the reaction solution is preferably about 0.1 to 0.7 U/mL.

In the method (3) above, the concentration of catalase in the reaction solution is preferably about 40 to 2500 U/mL.

The concentration in the peroxidase reaction solution is preferably about 0.4 to 2.0 U/mL.

In the method (2) or (3) above, the concentration of the electron donor used is preferably 0.1 mmol/L or more, and preferably 8 mmol/L or less at the final concentration in the reaction solution.

When the first reagent composition contains lipoprotein lipase, the concentration of the lipoprotein lipase in the reaction solution is preferably 0.01 U/mL or more, and preferably 10 U/mL or less, more preferably 5 U/mL or less, and even more preferably 1 U/mL or less.

In the first step, by leading cholesterol in L LDL and lipoproteins other than and LDL such as VLDL and HDL to the outside of the reaction system, in the subsequent step, preferably, only sdLDL remains in the reaction solution as a lipoprotein. In this manner, such procedures of removing lipoproteins other than sdLDL, leading the lipoproteins to the outside of the reaction system, so as to prevent the detection of cholesterol in lipoproteins other than sdLDL in the subsequent step may also be described as "differentiate sdLDL from lipoproteins other than sdLDL."

Further, in the first step, cholesterol in lipoproteins other than sdLDL may not be completely removed, and in this case, preferably, in the second step, a surfactant which makes it possible to selectively measure sdLDL-C may be used.

In addition, in the first step, at least one of a monovalent cation and a divalent cation or a salt thereof can be used as an ionic strength adjuster by further adding such ionic strength adjuster to the reaction solution. Addition of such ionic strength adjuster facilitates differentiation of sdLDL and L LDL.

Specifically, an ionic strength adjuster can be selected from the group consisting of chlorides such as sodium chloride, potassium chloride, magnesium chloride, manganese chloride, calcium chloride, lithium chloride, and ammonium chloride; sulfates such as magnesium sulfate, potassium sulfate, lithium sulfate, and ammonium sulfate; and acetates such as magnesium acetate and used. The concentration of the ionic strength adjuster in the reaction solution is preferably 0 to 100 mmol/L.

In addition, when the first reagent composition has sphingomyelinase activity, a polyanion can be added in the first step to adjust the catalytic activity of phospholipase on sdLDL and L LDL.

As the polyanion to be added, heparin, phosphotungstic acid, dextran sulfate, and the like can be suitably used. The concentration of the polyanion in the first reagent composition is preferably 10 to 250 U/mL in the case of heparin, 0.02% to 1.25% (w/v) in the case of phosphotungstic acid, and 0.02% to 1.25% (w/v) in the case of dextran sulfate. The concentrations of these polyanions in the reaction solution are preferably 5 to 250 U/mL, 0.01% to 1.25% (w/v), and 0.01% to 1.25% (w/v), respectively.

(Second Step)

In the second step, the sdLDL-C remaining after the first step is quantified. In the second step, a conventionally used LDL quantification method may be used. Examples of such method include a method of quantifying the content of LDL specific aggregates formed by adding an LDL coagulant by turbidimetric determination, a method of using an antigen-antibody reaction with an LDL specific antibody, and a method of quantifying degraded products using enzymes. Of these methods, a method of quantifying degraded products using enzymes is preferable.

In the method of quantifying degraded products using enzymes, for example, the second reagent composition containing one or two or more cholesterol measuring enzymes selected from the group consisting of cholesterol esterase, cholesterol oxidase, and cholesterol dehydrogenase is added to the reaction solution after the first step, and sdLDL-C is liberated and degraded to quantify the reaction products.

In addition, it is also preferable to use the second reagent composition containing a surfactant in the second step. When the second reagent composition contains a surfactant, the concentration of the surfactant in the reaction solution in the second step is preferably 0.01% (w/v) or more, and more preferably 0.1% (w/v) or more, and preferably 10% (w/v) or less, and more preferably 5% (w/v) or less.

In the embodiment, the reaction temperature in each step is preferably 2° C. to 45° C., and more preferably 25° C. to 40° C.

The reaction time is preferably 1 to 10 minutes for each step, and more preferably 3 to 7 minutes.

As an example of the sample used in the method of quantifying sdLDL-C, a sample derived from blood such as serum and blood plasma may be used.

Examples of the autoanalyzer to be used in the quantification of sdLDL-C include TBA-120FR and TBA-200FR (all manufactured by TOSHIBA Corporation), JCA-BM 1250, JCA-BM 1650, and JCA-BM 2250 (all manufactured by JEOL Ltd.), HITACHI 7180, and HITACHI 7170 (all manufactured by Hitachi, Ltd.), AU2700, AU5800, and AU680 (all manufactured by Olympus Corporation), and cobas c501 and cobas c701 (all manufactured by Roche).

The sdLDL-C is quantified by measuring the absorbance in a wavelength range of 580 to 720 nm, preferably 600 to 700 nm, for example.

Next, a method of measuring the enzyme activity of the first and second reagent compositions will be described.

In the embodiment, the cholesterol oxidase activity, cholesterol esterase activity, sphingomyelinase activity, peroxidase activity, and catalase activity of the reagent compositions can be measured by, for example, the following methods.

In the measurement of cholesterol oxidase activity, a 6 mM cholesterol solution (dissolved in isopropanol) is used as a substrate solution. A diluent (0.1 M phosphate buffer solution, Triton X100, pH 7.0) is added so that the concentration of the measurement target is 2 to 4 U/mL, 3 mL of the solution after dilution is heated at 37° C. for 5 minutes, and 0.05 mL of a substrate solution is added thereto. Then, the mixed solution is allowed to react at 37° C. and the amount of change in absorbance at a wavelength of 240 nm is measured. After the reaction at 37° C., the amount of change in absorbance from 2 minutes to 7 minutes is measured, and the cholesterol oxidase activity is calculated. For example, when the amount of change in absorbance is 3 U/L or more, it can be said that the measurement target has cholesterol oxidase activity, and more specifically, it can be said that cholesterol oxidase is contained.

In the measurement of cholesterol esterase activity, a substrate (0.04% cholesterol linolenate, 1% Triton X100, and 0.6% sodium cholate solution), a 300 U/mL cholesterol oxidase solution, an enzyme diluent (20 mM phosphate buffer solution, 0.5 mM EDTA 2Na, 2 mM MgcL$_2$, and 0.2% BSA, pH 7.5), and a reaction solution (0.06% 4-aminoantipyrine, 0.4% phenol, and 7.5 KU/L peroxidase) are used. Ater mixing 1.75 mL of the reaction solution and 1.0 mL of the substrate solution, the mixed solution is heated at 37° C. for 5 minutes, and a 0.1 mL cholesterol oxidase solution is added thereto. After heating the mixed solution at 37° C. for 2 minutes, 0.1 mL of the measurement target diluted with the diluent is added, the mixed solution is allowed to react at 37° C., and the amount of change in absorbance at a wavelength of 500 nm is measured. After the reaction at 37° C., the amount of change in absorbance from 0 minute to 3.5 minutes is measured, and the cholesterol esterase activity is calculated. For example, when the amount of change in absorbance is 8 U/L or more, it can be said that the measurement target has cholesterol esterase activity, and more specifically, it can be said that cholesterol esterase is contained.

In the measurement of sphingomyelinase activity, a reaction solution (0.008% sphingomyelin, 0.05% Triton X100 solution, 10 U/mL alkafine phosphatase, 10 U/mL cholesterol oxidase, 2 U/mL peroxidase, 0.02% 4-aminoantipyrine, and 0.02% TODB mixed solution), a reaction stop solution (1% sodium dodecyl sulfate solution), and a diluent (10 mM Tris buffer solution, and 0.1% Triton X100, pH 8.0) are used, 0.08 mL of the reaction solution and 0.003 mL of the measurement target diluted with the diluent are mixed, the mixed solution is heated at 37° C. for 5 minutes, and then 0.16 mL of the reaction stop solution is added thereto. After the reaction is stopped, the amount of change in absorbance at a main wavelength of 546 nm and a sub-wavelength of 700 nm is measured, and the sphingomyelinase activity is calculated. For example, when the amount of change in absorbance is 2 U/L or more, it can be said that the measurement target has sphingomyelinase activity, and more specifically, it can be said that sphingomyelinase is contained.

In the measurement of peroxidase activity, reaction solution 1 (1.5 mM HDAOS, 0.05% Triton X100, and 50 mM phosphate buffer solution, pH 7.0) and reaction solution 2 (5 mM 4-aminoantipyine, 0.05% Triton X100, 1% hydrogen peroxide, and 50 mM phosphate buffer solution, pH 7.0), and a diluent (50 mM phosphate buffer solution, pH 7.0) are used, 0.3 mL of the reaction solution 1 and 0.08 mL of the measurement target diluted with the diluent are mixed and the mixed solution is heated at 37° C. for 5 minutes. After that, 0.1 mL of the reaction solution 2 is added, and the reaction is carried out at 37° C. and the amount of change in absorbance at a main wavelength of 600 nm and a sub-wavelength of 700 nm is measured. After the reaction at 37° C., the amount of change in absorbance from 2 minutes to 5 minutes is measured to calculate the peroxidase activity. For example, when the amount of change in absorbance is 10 U/L or more, it can be said that the measurement target has peroxidase activity, and more specifically, it can be said that peroxidase is contained.

A substrate (0.06% hydrogen peroxide, and 50 mM phosphate buffer solution, pH 7.0) is used to measure catalase activity. After preheating 2.9 mL of the substrate solution at 25° C., the solution is mixed with 0.1 mL of the measurement target, and the amount of change in absorbance at 240 nm is measured. After the reaction at 25° C., the amount of change in absorbance from 0 to 3 minutes is measured to calculate the catalase activity. For example, when the amount of change in absorbance is 100 U/L or more, it can be said that the measurement target has catalase activity, and more specifically, it can be said that catalase is contained.

The enzymes in the first and second reagent compositions can also be identified by the following methods. That is, first, a fragment peptide obtained by degrading a sample containing a target enzyme with trypsin is detected by a hybrid mass spectrometer. Proteins can be identified by database search (for example, Mascot search) of the mass of peptides obtained using a mass spectrometer and the spectrum (MS/MS data) of fragment ions obtained by colliding with argon gas in the mass spectrometer. When the sequence of the fragment peptide derived from the amino acid sequence in the reagent composition matches with the amino acid sequence registered in the database as a unique sequence, it can be considered that the target enzyme is contained.

The enzymes in the first and second reagent compositions can also be identified by, for example, the following quantification. That is, among the fragment peptides obtained by degrading the target enzyme with trypsin, a peptide that is specific to the target enzyme and gives a strong signal in mass spectrometry is selected as a peptide to be quantified. For the peptide to be quantified, an unlabeled peptide and a peptide labeled with a stable isotope as an internal standard are prepared by chemical synthesis. A sample containing the target enzyme was completely digested with trypsin, a known amount of stable isotope-labeled peptide is added, and measurement is performed in a multiple reaction monitoring (MRM) mode with a triple quadrupole mass spectrometer (LC-MS/MS) connected to HPLC. A mixed solution of the unlabeled peptide of the peptide to be quantified and a known amount of stable isotope-labeled peptide is measured in the same manner to create a calibration curve of the concentration ratio and the peak area ratio of the internal standard, and the absolute amount of the peptide to be quantified in the sample is calculated. Thus, the target enzyme can be quantified.

Although the embodiments of the present invention have been described above, these are examples of the present invention, and various compositions other than the above can be adopted.

EXAMPLES

In each of the following examples, U-3900 manufactured by Hitachi, Ltd. was used for measuring the absorption spectrum.

First, the components used in the reagent composition will be described.

In the following examples, the first and second reagent compositions each were prepared by formulating each component listed in Table 1 or 2 in a PIPES buffer solution (50 mmol/L, pH 7.0) at the concentration listed in each table.

The components listed in Tables 1 and 2 are shown below.
TOOS: N-ethyl-N-(2-hydroxy-3-sulfopropyl)-3-methylaniline
4-AA: 4-Aminoantipyrine
FeK: Potassium ferrocyanide
POD: Peroxidase
B-Cat: Catalase
$NaN_3$: Sodium azide

Preparation Example 1

Examples 1-1 to 1-8 and Comparative Examples 1-1 to 1-4

The first reagent composition of each example was prepared with the formulation composition shown in Table 1.

Here, the first reagent composition of each example was assumed to contain the following components in common in addition to the components shown in Table 1.

(Common Components of First Reagent Composition)
Cholesterol esterase: 0.6 U/mL
Cholesterol oxidase: 0.5 U/mL
Sphingomyelinase: 2.7 U/mL
Polyoxyethylene polycyclic phenyl ether (manufactured by Kao Corporation): 0.3% (w/v)

The first reagent composition obtained was acceleratedly stored at 37° C. for 1 week or 2 weeks, and the absorption spectrum of the natural color development during storage was measured at a wavelength of 320 nm to 480 nm. Table 1 also shows the absorbance and the absorbance ratio of the reagent compositions obtained in each example.

In addition, FIGS. 1A to 1F and 2A to 2F show the absorption spectrums of the immediately after the preparation of the first reagent composition obtained in each example and after acceleratedly storing the first reagent composition at 37° C. for 1 week or 2 weeks.

TABLE 1

| | | | Example 1-1 | Example 1-2 | Example 1-3 | Example 1-4 | Example 1-5 | Example 1-6 |
|---|---|---|---|---|---|---|---|---|
| Reagent composition 1 | Formulation | TOOS | 2 mM | — | 2 mM | 2 mM | — | — |
| | | 4-AA | — | 1.3 mM | — | — | 1.3 mM | 1.3 mM |
| | | FeK | — | — | — | — | — | — |
| | | POD | — | — | 1.7 KU/L | 1.7 KU/L | 1.7 KU/L | 1.7 KU/L |
| | | B-Cat | 1200 KU/L | 1200 KU/L | — | 1200 KU/L | — | 1200 KU/L |
| | Absorbance after storage at 37° C. for 2 weeks | ABS450 | 0.0284 | 0.0636 | 0.0402 | 0.0372 | 0.0774 | 0.0775 |
| | | ABS400 | 0.0801 | 0.1316 | 0.1055 | 0.1028 | 0.1679 | 0.1729 |
| | | ABS360 | 0.2058 | 0.218 | 0.2879 | 0.2511 | 0.2582 | 0.2568 |
| | | R1 = ABS400/ABS450 | 2.82 | 2.07 | 2.62 | 2.76 | 2.17 | 2.23 |
| | | R2 = ABS360/ABS400 | 2.57 | 1.66 | 2.73 | 2.44 | 1.54 | 1.49 |

| | | | Example 1-7 | Comparative Example 1-1 | Example 1-8 | Comparative Example 1-2 | Comparative Example 1-3 | Comparative Example 1-4 |
|---|---|---|---|---|---|---|---|---|
| Reagent composition 1 | Formulation | TOOS | 2 mM | — | 2 mM | 2 mM | — | — |
| | | 4-AA | — | 1.3 mM | — | — | 1.3 mM | 1.3 mM |
| | | FeK | 0.036 mM | 0.036 mM | 0.036 mM | 0.036 mM | 0.036 mM | 0.036 mM |
| | | POD | — | — | 1.7 KU/L | 1.7 KU/L | 1.7 KU/L | 1.7 KU/L |
| | | B-Cat | 1200 KU/L | 1200 KU/L | — | 1200 KU/L | — | 1200 KU/L |
| | Absorbance after storage at 37° C. for 2 weeks | ABS450 | 0.0361 | 0.1261 | 0.0362 | 0.0377 | 0.1444 | 0.1453 |
| | | ABS400 | 0.1004 | 0.4394 | 0.1087 | 0.1183 | 0.5156 | 0.5191 |
| | | ABS360 | 0.2339 | 0.7461 | 0.2334 | 0.2405 | 0.8777 | 0.8765 |
| | | R1 = ABS400/ABS450 | 2.78 | 3.48 | 3.00 | 3.14 | 3.57 | 3.57 |
| | | R2 = ABS360/ABS400 | 2.33 | 1.70 | 2.15 | 2.03 | 1.70 | 1.69 |

Preparation Example 2

Examples 2-1 to 2-9 and Comparative Examples 2-1 to 2-4

The second reagent composition of each example was prepared with the formulation composition shown in Table 2.

Here, the second reagent composition of each example commonly contains the following components in addition to the components shown in Table 2.

(Common Components of Second Reagent Composition)
Polyoxyethylene alkyl ether (manufactured by Kao Corporation): 1.0% (w/v)

The second reagent composition obtained was acceleratedly stored at 37° C. for 1 week or 2 weeks, and the absorption spectrum of the natural color development during storage was measured at a wavelength of 320 nm to 480 nm. Table 2 also shows the absorbance and the absorbance ratio of the reagent compositions obtained in each example.

In addition, FIGS. 3A to 3F and 4A to 4G show the absorption spectrums of the immediately ater the preparation of the second reagent composition obtained in each example and alter acceleratedly storing the second reagent composition at 37° C. for 1 week or 2 weeks.

bance at a main wavelength of 600 nm to obtain an absorbance difference. Then, the average value of the blank absorbance difference was subtracted from the average value of the absorbance difference of the standard substance to calculate the calibration absorbance of each example.

TABLE 2

|  |  |  | Comparative Example 2-1 | Example 2-1 | Comparative Example 2-2 | Comparative Example 2-3 | Example 2-2 | Example 2-3 |
|---|---|---|---|---|---|---|---|---|
| Reagent composition 2 | Formulation | TOOS | — | 6 mM | — | — | 6 mM | 6 mM |
|  |  | 4-AA | 4 mM | — | 4 mM | 4 mM | — | — |
|  |  | FeK | 0.109 mM | 0.109 mM | 0.109 mM | 0.109 mM | 0.109 mM | 0.109 mM |
|  |  | POD | 5 KU/L | 5 KU/L | — | — | — | — |
|  |  | NaN$_3$ | 0.05% | 0.05% | — | 0.05% | — | 0.05% |
|  | Absorbance after storage at 37° C. for 2 weeks | ABS450 | 0.2005 | 0.0308 | 0.1414 | 0.1348 | 0.0214 | 0.0211 |
|  |  | ABS400 | 2.3506 | 0.0933 | 1.4446 | 1.4376 | 0.0449 | 0.0367 |
|  |  | ABS360 | 4.6621 | 0.1218 | 2.5307 | 2.7513 | 0.0992 | 0.0792 |
|  |  | R1 = ABS400/ABS450 | 11.72 | 3.03 | 10.22 | 10.66 | 2.10 | 1.74 |
|  |  | R2 = ABS360/ABS400 | 1.98 | 1.31 | 1.75 | 1.91 | 2.21 | 2.16 |

|  |  |  | Example 2-4 | Example 2-5 | Example 2-6 | Example 2-7 | Example 2-8 | Example 2-9 | Comparative Example 2-4 |
|---|---|---|---|---|---|---|---|---|---|
| Reagent composition 2 | Formulation | TOOS | — | 6 mM | — | — | 6 mM | 6 mM | — |
|  |  | 4-AA | 4 mM | — | 4 mM | 4 mM | — | — | 4 mM |
|  |  | FeK | — | — | — | — | — | — | 0.109 mM |
|  |  | POD | 5 KU/L | 5 KU/L | — | — | — | — | 5 KU/L |
|  |  | NaN$_3$ | 0.05% | 0.05% | — | 0.05% | — | 0.05% | — |
|  | Absorbance after storage at 37° C. for 2 weeks | ABS450 | 0.0354 | 0.0188 | 0.0218 | 0.0231 | 0.0067 | 0.0079 | 0.2217 |
|  |  | ABS400 | 0.2255 | 0.0783 | 0.1178 | 0.127 | 0.0231 | 0.0185 | 2.4192 |
|  |  | ABS360 | 0.2243 | 0.1013 | 0.1238 | 0.137 | 0.061 | 0.0439 | 4.3197 |
|  |  | R1 = ABS400/ABS450 | 6.37 | 4.16 | 5.40 | 5.50 | 3.45 | 2.34 | 10.91 |
|  |  | R2 = ABS360/ABS400 | 0.99 | 1.29 | 1.05 | 1.08 | 2.64 | 2.37 | 1.79 |

Examples 3-1 to 3-4 and Comparative Examples 3-1 to 3-7

The first and second reagent compositions in each example were stored at 37° C. for 2 weeks, and an acceleration test was performed.

The first and second reagent compositions after storage were used in the combinations shown in Tables 3 to 5, and it was evaluated whether or not sdLDL could be accurately quantified. The evaluation results are also shown in Tables 3 to 5.

(Catalase System)

Table 3 shows the results of a measurement system in which the first and second reagent compositions were combined so as to remove cholesterol in lipoproteins other than sdLDL with catalase.

In each measurement system, a calibration absorbance was measured by the following method. Here, the calibration absorbance is the absorbance at the measurement wavelength in the case where a standard substance having a known sdLDL-C concentration is measured.

That is, for the standard substance having an sdLDL-C concentration of 41 mg/dL and the physiological saline solution which is a blank substance in which sdLDL-C does not exist, the sdLDL-C concentration was measured three times by the following method, and the absorbance at a sub-wavelength of 700 nm was subtracted from the absor- Specifically, for each example shown in Table 3, the sdLDL-C concentration was measured and evaluated according to the following procedure.

(Measurement and Evaluation Method of sdLDL-C Concentration)

1. To 3.0 µL of the above standard substance and physiological saline solution sample, 150 µL of the first reagent composition of each example was added and allowed to act at 37° C. for 5 minutes.
2. To a sample obtained in the above 2., 50 µL of the second reagent composition of each example was added and allowed to act at 37° C. for 5 minutes.
3. The absorbances of the sample obtained in the above 2, at wavelengths of 600 nm and 700 nm immediately before the second reagent composition was added and alter 5 minutes from the addition of the second reagent composition were measured and the calibration absorbance was calculated from (absorbance at 600 nm after 5 minutes from the addition of the second reagent composition—absorbance at 700 nm)—(absorbance at 600 nm immediately before the second reagent composition was added—absorbance at 700 nm).
4. On the other hand, the measurement accuracy of each example was evaluated in such a manner that the case where the measurement result of the sdLDL-C concentration was 41±2.1 mg/dL was evaluated as "O", and the case where the measurement result was out of the above range was evaluated as "x".

TABLE 3

Catalase system

|  | Comparative Example 3-1 | Example 3-1 | Example 3-2 | Comparative Example 3-2 |
|---|---|---|---|---|
| First reagent composition | Example 1-1 | Example 1-2 | Example 1-7 | Comparative Example 1-1 |
| Second reagent composition | Comparative Example 2-1 | Example 2-1 | Example 2-4 | Example 2-5 |
| Calibration absorbance after storage for 2 weeks (mABS) | 72.4 | 73.1 | 77.3 | 71.4 |
| Evaluation | x | ○ | ○ | x |

From each example shown in Table 3, in the measurement system for removing cholesterol in lipoproteins other than sdLDL with catalase, the calibration absorbance range capable of accurately measuring sdLDL-C was 73 mABS or more and 120 mABS or less. Here, the calibration absorbance range is an index showing the accuracy in quantification of sdLDL-C.

In addition, in Examples in which R1 of both the first and second reagent compositions was within a specific range, sdLDL-C could be accurately measured.

(Colorless Quinone System)

Table 4 shows the results of a measurement system in which the first and second reagent compositions are combined so that the first reagent composition contains peroxidase, forms a colorless quinone and removes cholesterol in lipoproteins other than sdLDL.

For each example shown in Table 4, the sdLDL-C concentration was measured and evaluated according to the above-mentioned method in Table 3.

TABLE 4

Colorless quinone system

|  | Comparative Example 3-3 | Example 3-3 | Comparative Example 3-4 |
|---|---|---|---|
| First reagent composition | Example 1-3 | Example 1-5 | Comparative Example 1-3 |
| Second reagent composition | Comparative Example 2-2 | Example 2-2 | Example 2-3 |
| Calibration absorbance after storage for 2 weeks (mABS) | 88 | 191 | 197 |
| Evaluation | x | ○ | x |

From each example shown in Table 4, in the measurement system for removing cholesterol in lipoproteins other than sdLDL with colorless quinone, the calibration absorbance range capable of accurately measuring sdLDL-C was 150 mABS or more and 195 mABS or less.

In addition, in Examples in which R1 of both the first and second reagent compositions was within a specific range, sdLDL-C could be accurately measured.

(Hybrid Removing System)

Table 5 shows the result of the combination of the first and second reagent compositions as a hybrid removing system in which the first reagent composition contains peroxidase, forms a colorless quinone to remove cholesterol in lipoproteins other than sdLDL, and removes cholesterol in lipoproteins other than sdLDL with catalase.

For each example shown in Table 5, the sdLDL-C concentration was measured and evaluated according to the above-mentioned method in Table 3.

TABLE 5

Hybrid removing system

|  | Comparative Example 3-5 | Example 3-4 | Comparative Example 3-6 | Comparative Example 3-7 |
|---|---|---|---|---|
| First reagent composition | Example 1-4 | Example 1-6 | Comparative Example 1-2 | Comparative Example 1-4 |
| Second reagent composition | Comparative Example 2-3 | Example 2-3 | Example 2-7 | Example 2-9 |
| Calibration absorbance after storage for 2 weeks (mABS) | 78 | 158 | 190 | 164 |
| Evaluation | x | ○ | x | x |

From each example shown in Table 5, in the measurement system for removing cholesterol in lipoproteins other than sdLDL with catalase and colorless quinone, the calibration absorbance range capable of accurately measuring sdLDL-C was 110 mABS or more and 160 mABS or less.

In addition, in Examples in which R1 of both the first and second reagent compositions was within a specific range, sdLDL-C could be accurately measured.

This application claims priority on the basis of Japanese Patent Application No. 2019-164200 filed on Sep. 10, 2019, the entire disclosure of which is incorporated herein.

The invention claimed is:

1. A kit used for fractionation of small dense LDL cholesterol (sdLDL-C) in a sample, comprising:
    a first reagent composition having one or two or more activities selected from the group consisting of cholesterol esterase activity, cholesterol oxidase activity, and sphingomyelinase activity; and
    a second reagent composition for quantifying the sdLDL-C,
    wherein in an absorption spectrum after storing the first reagent composition at 37° C. for 2 weeks, when an absorbance at a wavelength of 400 nm is ABS400, and an absorbance at a wavelength of 450 nm is ABS450, a ratio R1 represented by ABS400/ABS450 is 0.90 or more and 3.00 or less,
    wherein in an absorption spectrum after storing the second reagent composition at 37° C. for 2 weeks, when an absorbance at a wavelength of 400 nm is ABS400 and an absorbance at a wavelength of 450 nm is ABS450, a ratio R1 represented by ABS400/ABS450 is 0.90 or more and 8.00 or less,
    wherein the first reagent composition satisfies one or two conditions of Conditions 1 to 3, and
    wherein the second reagent composition does not satisfy the one or two conditions of Conditions 1 to 3 and satisfies all other conditions,
    wherein Condition 1=comprises a coupler;
    wherein Condition 2=comprises an iron complex; and
    wherein Condition 3=possesses a peroxidase activity.

2. The kit according to claim 1, wherein in the absorption spectrum after storing the first reagent composition at 37° C. for 2 weeks, when an absorbance at a wavelength of 360 nm is ABS360, a ratio R2 represented by ABS360/ABS400 is 0.90 or more and 2.50 or less.

3. The kit according to claim 1, wherein the first reagent composition further has catalase activity.

4. The kit according to claim 1, wherein the first reagent composition contains a surfactant that acts on lipoproteins other than the small dense LDL (sdLDL).

5. The kit according to claim 1, wherein in the absorption spectrum after storing the second reagent composition at 37° C. for 2 weeks, when an absorbance at a wavelength of 360 nm is ABS360, a ratio R2 represented by ABS360/ABS400 is 0.90 or more and 2.50 or less.

6. The kit according to claim 1, wherein the second reagent composition contains a surfactant that acts on the small dense LDL (sdLDL).

7. A method of quantifying small dense LDL cholesterol (sdLDL-C) in a sample, comprising:
  (a) allowing a first reagent composition having one or two or more activities selected from the group consisting of cholesterol esterase activity, cholesterol oxidase activity, and sphingomyelinase activity to act on the sample; and
  (b) allowing a second reagent composition for quantifying the sdLDL-C to act to quantify cholesterol in a remaining lipoprotein,
  wherein in an absorption spectrum after storing the first reagent composition at 37° C. for 2 weeks, when an absorbance at a wavelength of 400 nm is ABS400, and an absorbance at a wavelength of 450 nm is ABS450, a ratio R1 represented by ABS400/ABS450 is 0.90 or more and 3.00 or less,
  wherein in an absorption spectrum after storing the second reagent composition at 37° C. for 2 weeks, when an absorbance at a wavelength of 400 nm is ABS400 and an absorbance at a wavelength of 450 nm is ABS450, a ratio R1 represented by ABS400/ABS450 is 0.90 or more and 8.00 or less,
  wherein the first reagent composition satisfies one or two conditions of Conditions 1 to 3, and
  wherein the second reagent composition does not satisfy the one or two conditions of Conditions 1 to 3 and satisfies all other conditions,
  wherein Condition 1=comprises a coupler,
  wherein Condition 2=comprises an iron complex; and
  wherein Condition 3=possesses a peroxidase activity.

8. The method according to claim 7, wherein in the absorption spectrum after storing the first reagent composition at 37° C. for 2 weeks, when an absorbance at a wavelength of 360 nm is ABS360, a ratio R2 represented by ABS360/ABS400 is 0.90 or more and 2.50 or less.

9. The method according to claim 7, wherein the first reagent composition further has catalase activity.

10. The method according to claim 7, wherein the first reagent composition contains a surfactant that acts on lipoproteins other than the sdLDL.

11. The method according to claim 7, wherein in the absorption spectrum after storing the second reagent composition at 37° C. for 2 weeks, when an absorbance at a wavelength of 360 nm is ABS360, a ratio R2 represented by ABS360/ABS400 is 0.90 or more and 2.50 or less.

12. The method according to claim 7, wherein the second reagent composition contains a surfactant that acts on the sdLDL.

* * * * *